United States Patent
Bridges, III et al.

(10) Patent No.: US 7,459,700 B2
(45) Date of Patent: Dec. 2, 2008

(54) ANTHRAX REMEDIATION AND RESPONSE

(75) Inventors: John H. Bridges, III, Stafford, VA (US); Dennis Baca, Gainesville, VA (US)

(73) Assignee: United States Postal Service, Washington, DC (US)

( * ) Notice: Subject to any disclaimer, the term of this patent is extended or adjusted under 35 U.S.C. 154(b) by 526 days.

(21) Appl. No.: 10/422,708

(22) Filed: Apr. 24, 2003

(65) Prior Publication Data

US 2004/0061076 A1     Apr. 1, 2004

Related U.S. Application Data

(60) Provisional application No. 60/374,813, filed on Apr. 24, 2002.

(51) Int. Cl.
    *G21G 5/00*     (2006.01)
    *A61N 5/00*     (2006.01)

(52) U.S. Cl. .................... 250/492.1; 422/37

(58) Field of Classification Search ............. 250/492.3; 232/30
See application file for complete search history.

(56) References Cited

U.S. PATENT DOCUMENTS

| | | | |
|---|---|---|---|
| 4,272,019 A | 6/1981 | Halaby, Jr. ............... | 239/8 |
| 4,681,739 A | 7/1987 | Rosenblatt et al. ........ | 422/37 |
| 4,780,333 A | 10/1988 | Smith et al. ............. | 427/236 |
| 5,261,460 A * | 11/1993 | Rupp .................... | 137/883 |
| 5,547,312 A * | 8/1996 | Schmitz, Jr. ............ | 405/52 |
| 5,603,972 A * | 2/1997 | McFarland .............. | 426/240 |
| 5,738,778 A | 4/1998 | Doring ................. | 205/701 |
| 5,998,691 A | 12/1999 | Abel et al. ............. | 588/201 |
| 6,233,748 B1 | 5/2001 | Gieger et al. ............ | 2/410 |
| 6,327,812 B1 | 12/2001 | Hedman et al. .......... | 43/124 |
| 6,485,683 B1 * | 11/2002 | Walles .................. | 422/4 |
| 6,537,821 B1 | 3/2003 | Rosenblatt et al. ........ | 436/124 |

(Continued)

FOREIGN PATENT DOCUMENTS

WO     WO 01/94256     12/2001

(Continued)

OTHER PUBLICATIONS

USPS News; press Release No. 01-093, USPS Awards Contract To Ion Beam Applications Inc. To Sanitize Mail,Nov. 2, 2001.*

(Continued)

*Primary Examiner*—Jack I Berman
*Assistant Examiner*—Andrew Smyth
(74) *Attorney, Agent, or Firm*—Finnegan, Henderson, Farabow, Garrett & Dunner (57) ABSTRACT

Remediation methods in response to a biological attack address treatment of goods (e.g., mail items), vehicle interiors, facilities, and personal protective equipment. The treatment of mail involves segregation of mail items by size and the organization and packaging of the segregated mail items for exposure to accelerated electron beam irradiation. Vehicle interiors are cleaned in a suitable decontamination area with a bleach solution. Facilities are separated into an exclusion zone, adjacent contamination reduction zone, and adjacent support zone. Persons enter the exclusion zone wearing personal protective equipment, exit the exclusion zone and enter the contamination reduction zone, and de-contaminate their personal protective equipment in the contamination reduction zone utilizing a bleach solution.

24 Claims, 4 Drawing Sheets

U.S. PATENT DOCUMENTS

| | | | |
|---|---|---|---|
| 6,613,571 B2 | 9/2003 | Cordery et al. | 436/48 |
| 6,635,676 B2 | 10/2003 | Baker, Jr. et al. | 514/642 |
| 6,646,270 B2 | 11/2003 | Cunningham | 250/455.11 |
| 6,653,519 B2 | 11/2003 | Koper et al. | 588/200 |
| 6,656,919 B1 | 12/2003 | Baugh et al. | 514/46 |
| 6,660,227 B2 | 12/2003 | Lopez Ordaz | 422/24 |
| 6,687,640 B1 | 2/2004 | Gelbard | |
| 6,928,143 B2* | 8/2005 | Menear et al. | 378/69 |
| 7,067,089 B2* | 6/2006 | Wen | 422/292 |
| 7,131,236 B2 | 11/2006 | Sample et al. | |
| 7,153,471 B2 | 12/2006 | Weinberg et al. | |
| 7,265,253 B2* | 9/2007 | Mielnik et al. | 588/299 |
| 2002/0124664 A1 | 9/2002 | Call et al. | |
| 2002/0125196 A1 | 9/2002 | Rosenblatt et al. | |
| 2002/0150500 A1 | 10/2002 | Carman et al. | |
| 2003/0037812 A1* | 2/2003 | Stewart et al. | 135/96 |
| 2003/0124025 A1* | 7/2003 | Mize et al. | 422/28 |
| 2003/0127505 A1* | 7/2003 | Avant | 232/30 |
| 2003/0138371 A1 | 7/2003 | McWhorter et al. | |
| 2003/0143111 A1 | 7/2003 | Cowley et al. | |
| 2004/0022665 A1* | 2/2004 | Lu | 422/1 |
| 2004/0022679 A1 | 2/2004 | St. Onge et al. | |
| 2004/0177447 A1* | 9/2004 | Love | 5/658 |
| 2004/0208282 A1* | 10/2004 | Menear et al. | 378/64 |

FOREIGN PATENT DOCUMENTS

| | | |
|---|---|---|
| WO | WO 02/072484 | 9/2002 |
| WO | WO 03/047640 | 6/2003 |
| WO | WO 03/059401 | 7/2003 |
| WO | WO 03/062144 | 7/2003 |
| WO | WO 03/077956 | 9/2003 |
| WO | WO 03/082353 | 10/2003 |

OTHER PUBLICATIONS

Bridges, USPS Operational Procedure EMP 2001-00 B-042 Dec. 3, 2001, paragraph 3.1.*

US Army Field Manual FM 3-3/FMFM 11-17 Chemical and Biological Contamination Avoidance (hereinafter FM 3-3/FMFM 11-17);Nov. 16, 1992.*

Notification of Transmittal of the International Search Report or the Declaration dated Jul. 28, 2005 from International Application No. PCT/US03/36080.

U.S. Appl. No. 10/882,214, filed Jul. 2, 2004, John H. Bridges III et al., System and Method for Decontamination.

U.S. Appl. No. 10/684,635, filed Oct. 14, 2003, John H. Bridges III, Anthrax Remediation and Response.

U.S. Appl. No. 60/324,908 of U.S. Patent No. 7,131,236: Sample et al., Portable Decontamination System, Sep. 27, 2002.

U.S. Appl. No. 60/346,282 of U.S. Patent No. 7,153,471: Weinberg et al., Method of Decontamination of Whole Structures and Articles Contaminated by Pathogenic Spores.

* cited by examiner

ANTHRAX REMEDIATION AND RESPONSE

RELATED APPLICATION

This non-provisional application claims priority from provisional application No. 60/374,813, filed on Apr. 24, 2002.

FIELD OF THE INVENTION

This invention relates generally to methods for responding to bioterrorism attacks and, more specifically, relates to a method or methods for responding to a bioterrorism attack that addresses the de-contamination of goods, vehicles, facilities, and personal protection equipment that are at least potentially contaminated as a result of such an attack and/or its remediation.

BACKGROUND OF THE INVENTION

In 2001, the world witnessed the danger posed by a bioterrorism attack. Beginning in the fall of 2001, a series of letters containing spores from the bacterium *Bacillus anthracis* were sent through the U.S. Postal system. Handlers and recipients of certain of these letters contracted anthrax, with more than 20 becoming ill and five dying.

This incident posed a number of challenges to those tasked with the responsibility for remediation. These included: (a) devising a method for treating mail that had either been exposed to anthrax spores, or where there was at least a concern of potential exposure; (b) devising and demonstrating a method for decontaminating vehicles used to transport such mail for decontamination or otherwise; (c) decontaminating a facility where there has been a bioterrorism attack or at least the possibility of one; and (d) devising a decontamination method for persons (including specifically their protective gear) who are required to enter a facility where there has been a possible bioterrorism attack.

These methods address the need for effective responses to bioterrorism. They have application not only to mail items, vehicles and facilities, but to other targets of bioterrorism. Further, they have application to anthrax-type bioterrorism attacks, as well as attacks utilizing other biological agents.

SUMMARY OF THE INVENTION

It is an object of the present invention to provide a remediation method in response to a bioterrorism attack, and in particular to treat goods, such as mail items, that have at least potentially been exposed to such an attack.

It is a yet further object of the present invention to provide a method in response to a bioterrorism attack, and in particular to treat vehicles that have at least potentially been exposed to such an attack.

It is a still further object of the present invention to provide a method in response to a bioterrorism attack, and in particular to decontaminate a facility that has at least potentially been exposed to such an attack.

It is a yet further object of the present invention to provide a method in response to a bioterrorism attack, and in particular to decontaminate persons (including specifically their protective gear) who are required to enter a facility that has at least potentially been exposed to such an attack.

DETAILED DESCRIPTION OF THE PREFERRED EMBODIMENTS

A bioterrorism attack poses a number of challenges for a proper and comprehensive response. While at least certain of the methods disclosed herein have been utilized in connection with a response to an anthrax-type of attack, it should be noted that they could be utilized with other biological agents. In this regard, the following is a classification of biological agents which may be used as bioweapons, and for which remediation as herein described is believed and now proven effective:

1. Bacteria—bacteria are small free-living organisms, most of which may be grown on solid or liquid culture media. They have a structure generally consisting of nuclear material disposed within cytoplasm, and are bounded by a cell membrane. Bacteria reproduce by simple division. The diseases that bacteria produce often respond to specific therapy with antibiotics.

*Bacillus anthracis* is an example of a bacteria type of biological agent. It was the first bacterium shown to be the cause of a disease. It most commonly occurs in wild and domestic lower vertebrates, such as cattle, sheep, goats, camels, antelopes and other herbivores. It can also occur in humans, typically when they are exposed to infected animals or to tissue from infected animals. The disease is acquired by skin contact with the bacteria or by inhaling the bacteria spores. The spores are capable of attaching to the clothing of a person who has entered a contaminated area.

Anthrax infection can occur in three forms: cutaneous, inhalation, and gastrointestinal. Cutaneous anthrax occurs after the bacteria contact skin cuts or abrasions. Usually within two weeks, an itchy skin lesion develops that is similar to an insect bite. This lesion may later blister and then break down, resulting in a black, frequently painless, ulcer. In 20% of cases where the individual is untreated, the infection may spread through the bloodstream and become fatal. Otherwise, with treated individuals, death from cutaneous anthrax is extremely rare.

Inhalation anthrax develops when anthrax spores enter the lungs. Development of the actual disease occurs after the spores germinate, a process that may take up to 60 days. Once the spores germinate, several toxic substances are released. This results in hemorrhage, swelling, and tissue death. In the first stage of inhalation anthrax, the individual can experience fever, headache, cough, shortness of breath, and chest pain. The second stage develops suddenly, and is characterized by shortness of breath, fever, and shock. Most of these cases are fatal.

Gastrointestinal anthrax occurs with ingestion of contaminated meat. Disease in these cases usually develops within one week and can affect the upper portion of the gastrointestinal tract or the intestines and colon. The infection can enter the bloodstream and result in death.

2. Viruses—Viruses are organisms that require living cells in which to replicate, and are therefore dependent upon the cells of the host that they infect. Their stability in the environment is very variable. They produce diseases which generally do not respond to antibiotics, but which may be responsive to anti-viral compounds. Supportive care (e.g., fluids, anti-inflammatories and rest) is often the only treatment for viral infections.

3. Rickettsiae—these are microorganisms that have characteristics common to both bacteria and viruses. Like bacteria, they possess metabolic enzymes and cell membranes, utilize oxygen and are susceptible to broad-spectrum antibiotics. They resemble viruses, on the other hand, in that they grow only within living cells.

4. Chlamydia—these are obligatory intracellular parasites that are incapable of generating their own energy source. Like bacteria, they are susceptible to broad-spectrum antibiotics. Like viruses, they require living cells for multiplication.

5. Fungi—these are primitive plants that utilize photosynthesis, are capable of anaerobic growth, and that draw nutrition from decaying vegetable matter. Most fungi form spores. Free-living forms are found in the soil. Fungal diseases may respond to various anti-microbial drugs.

6. Toxins—these are poisons that are produced by organisms. Toxins do not grow or reproduce. They are more easily controlled than live organisms. The potency of most toxins are such that very small doses will cause illness and/or death.

Evidence of a biological attack utilizing a biological agent can come in a number of ways. It is possible that the actual bioterror delivery system (e.g., the release of powdered material from processed mail or packages) may be observed. It can also come from the observance of any of the following:

1. Unusual number of casualties—A large number of casualties within a 48 to 72 hour period suggests that there may have been an attack with a microorganism. If the casualties occur within minutes to an hour of each other, a toxin is a more likely suspect. A large number of clinical cases relative to the number of exposed individuals, or other epidemiological evidence of a massive single source disease outbreak may all be indicative of a bioterror attack.

2. Unusual distribution of casualties—A high number of persons afflicted with respiratory illness, or a casualty distribution that is related to wind direction, might indicate that an aerosol attack has occurred. This could be corroborated by evidence of lower casualty rates among those working indoors, and in particular in areas with filtered air or closed ventilation systems.

3. Unusual distribution—A large number of rapidly fatal cases, with few recognizable signs and symptoms, may indicate exposure to multiple lethal doses of a biological agent from a single source.

4. Unusual disease pattern—The disease pattern associated with an attack utilizing a biological agent is likely to differ from those of a naturally occurring epidemic. For example, except for food borne outbreaks, disease incidence in naturally occurring epidemics usually increases over a period of weeks or months. However, in a bioterrorism attack, the increase in disease incidence may be only hours or days. Furthermore, instead of the usual peaks and troughs evidenced in most natural outbreaks, a steady and increasing stream of patients will be seen in a bioterror attack, similar to a food poisoning outbreak.

5. Unusual disease outbreak—the recurrence of a vector-borne disease without the vector (e.g., a mosquito or a tick) or the occurrence of a disease that is highly unusual for the geographic area could indicate that a bioterrorism attack has occurred.

6. Unusual disease symptoms—An unusually high prevalence of respiratory disease (e.g., pneumonia) from a disease that more often occurs naturally as a skin disease (e.g., inhalation in a natural outbreak) can be indicative of a bioterrorism attack.

7. Illness in animals and humans—an increased number of sick or dead animals, often of different species (e.g., rodents and dogs) at the same time as an increased number of human illness can be indicative of a bioterrorism attack.

Where a biological attack has occurred at a site such as a mail facility, those tasked with the remediation effort typically need to address remediation for exposed goods (e.g., mail items), for vehicles utilized in the response effort, for facilities where an attack has (or may have) occurred, and for persons (including their personal gear) who are involved in the remediation effort.

For goods of relatively small size, such as mail items, exposure to accelerated electron beam irradiation with sufficient intensity and for a sufficient period of time can kill anthrax spores and thus decontaminate the goods. (Such treatment is widely used for sterilizing medical instruments, cosmetics, and pharmaceuticals—in a non-bioterrorism context.) Testing has shown that such treatment does not produce or store any radiation in the treated goods. Moreover, it appears to produce no adverse health effects.

Turning particularly to a discussion of mail items suspected of contamination, it is preferred to arrange the mail items in a manner that will both ease their transportation (where this is necessary) and, more importantly, will optimize the efficiency of the irradiation treatment. First, it is desired to segregate mail items both by size and based on the contents thereof. Letter-size mail items (commonly referred to as "letter mail"), i.e., those having a height of four inches or less, a length of no more than 11 and ½ inches long, and a thickness of no more than ¼ inch, may be optimally processed as hereinafter described. However, of these mail items, it will be desired to separate out letter-size mail items containing plastics, credit-cards, compact disks and the like for alternative processing, because the method described herein has been shown to be harmful to such items.

The mail items should be positioned in a letter tray having a height of four inches. The mail items should be placed horizontally (i.e., flat) within the tray, and can be stacked to the height of the tray walls. However, care should be taken so that mail items are not positioned above the height of the walls.

The next step in the method is to place the filled tray into a letter tray sleeve. The letter tray sleeve is preferably closed by taping it along its length. The purpose of the letter tray sleeve is to maintain the letters in position within the tray.

The sleeve, with the filled tray therein, is next inserted into a polyvinyl bag having a thickness of between about 3 and about 6 mils. The bag is then tied, preferably by goosenecking (i.e. twisting) the opening and sealing it with duct tape. This sealed bag should then be inserted gooseneck-end first into a second polyvinyl bag, also having a thickness of between about 3 and about 6 mils. The second bag is sealed in like manner to the first—i.e., by goosenecking the end and sealing it with duct tape.

It is next preferred to insert the double-bagged letter tray into a cardboard box of sufficient dimension to receive the bagged tray, for purposes of securing it for travel. For a standard letter tray, the desired box dimensions are as follows: (a) interior dimensions: 12 inches wide, 26 inches long, and 6.75 inches deep; (b) exterior dimensions: 12.25 inches wide, 26.5 inches long, and 7 inches deep. The box must then be sealed, preferably by taping it shut with packing-type tape, preferably having a width of about 2 to 3 inches. (Duct tape is not preferred for box-sealing purposes.) At a minimum, the packing tape should be placed entirely around the width of the box.

Flat mail may be processed in a similar manner. As used herein, "flat mail" refers to mail having a length greater than 11.5 long, a thickness greater than 0.25 inch, a weight less than 13 ounces, and that will fit in a 10×14 envelope. "Flat mail typically includes periodicals and folded newspapers. As with the letter mail, it will be desired to separate out flat mail items containing plastics, credit-cards, compact disks and the like for alternative processing, because the method described herein has been shown to be harmful to such items.

The flat mail items should be stacked to a height not to exceed four inches. The next step in the method is to place the stacked flat mail into a polyethylene bag having a minimum thickness of between about 3 and about 6 mils. The air is gently pushed out of the bag. The bag is then tied, preferably by goosenecking (i.e. twisting) the opening, folding over the gooseneck, and sealing the bag tightly with duct tape. This sealed bag should then be inserted gooseneck-end first into a second polyvinyl bag, also having a minimum thickness of between about 3 and about 6 mils. The second bag is sealed in like manner to the first—i.e., by goosenecking the end and sealing it with duct tape.

For flat mail processing, it is next preferred to insert two double-bagged flat mail packages into a cardboard box of sufficient dimension to receive the bagged flat mail, for purposes of securing it for travel. The desired box dimensions for flat mail are as follows: (a) interior dimensions: 12 inches wide, 26 inches long, and 4.0 inches deep; (b) exterior dimensions: 12.25 inches wide, 26.5 inches long, and 4 inches deep. The box must then be sealed, preferably by taping it shut with packing-type tape, such as clear nylon tape, preferably having a width of about 2 to 3 inches. (Duct tape is not preferred for box-sealing purposes.) At a minimum, the packing tape should be placed entirely around the width of the box.

Where the irradiation equipment is located remote from the facility where the mail has been packaged, the sealed boxes are loaded onto vehicles for transport to the treatment location.

At the treatment location, the sealed boxes are exposed to accelerated electron beam irradiation for a time period that is between approximately 30 minutes and approximately 1 hour. This amount of time has been shown to be optimal for decontamination purposes.

Figure 1:
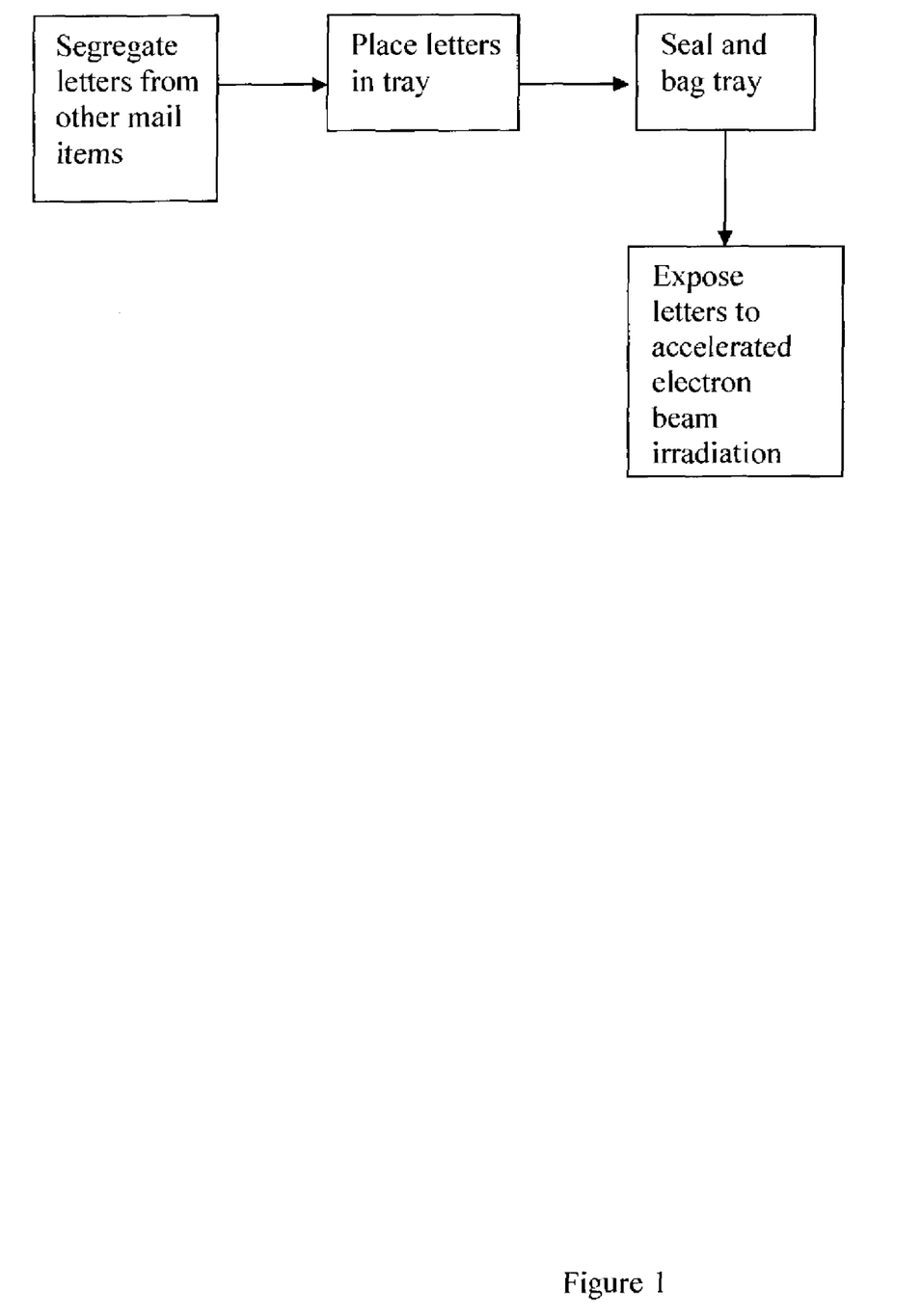
FIG. 1 is a flow chart illustrating the treatment of mail items suspected of exposure to a biological agent.
Figure 2:
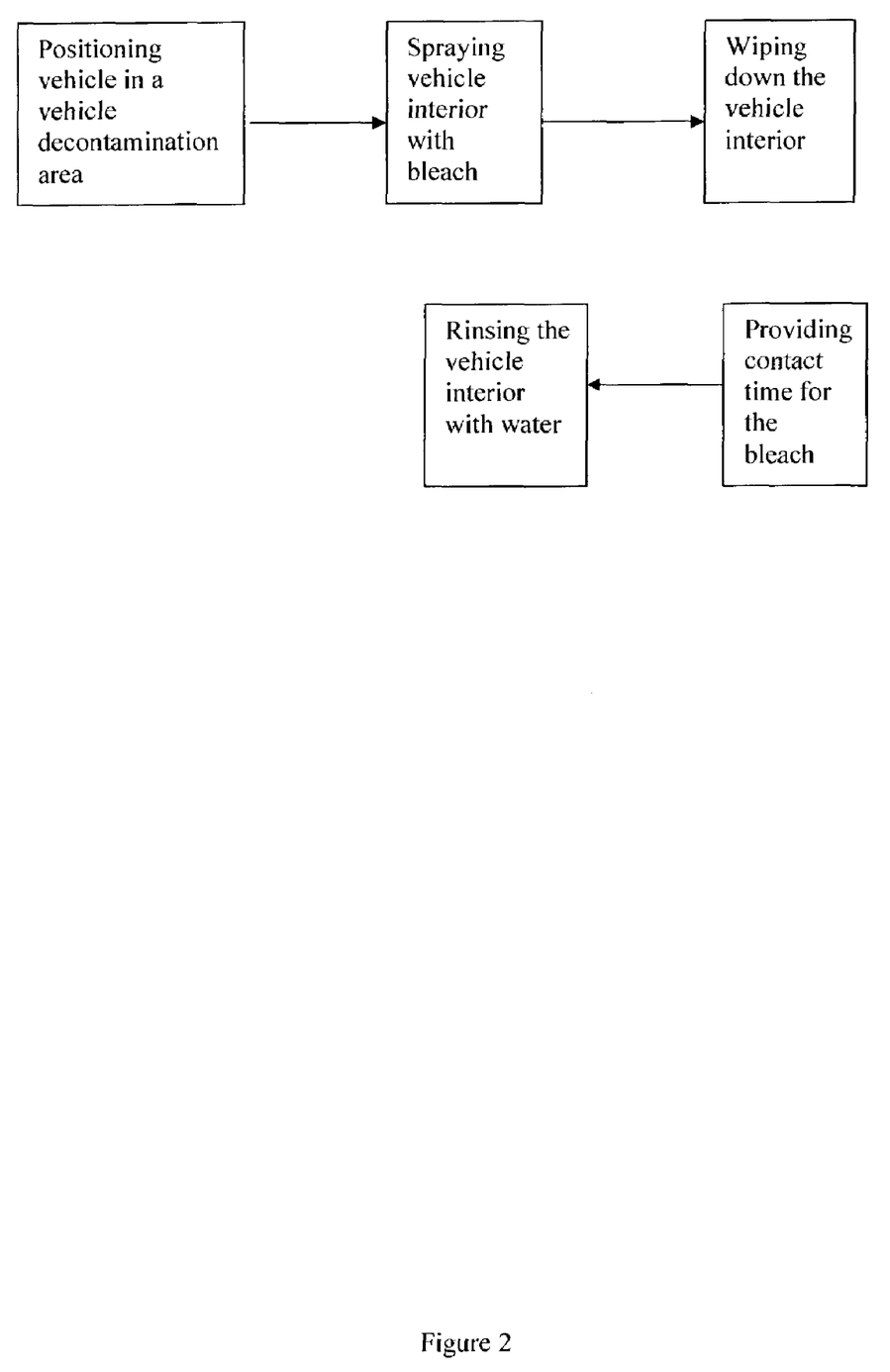
FIG. 2 is a flow chart illustrating the remediation of a vehicle interior possibly exposed to a biological agent.
Figure 3:
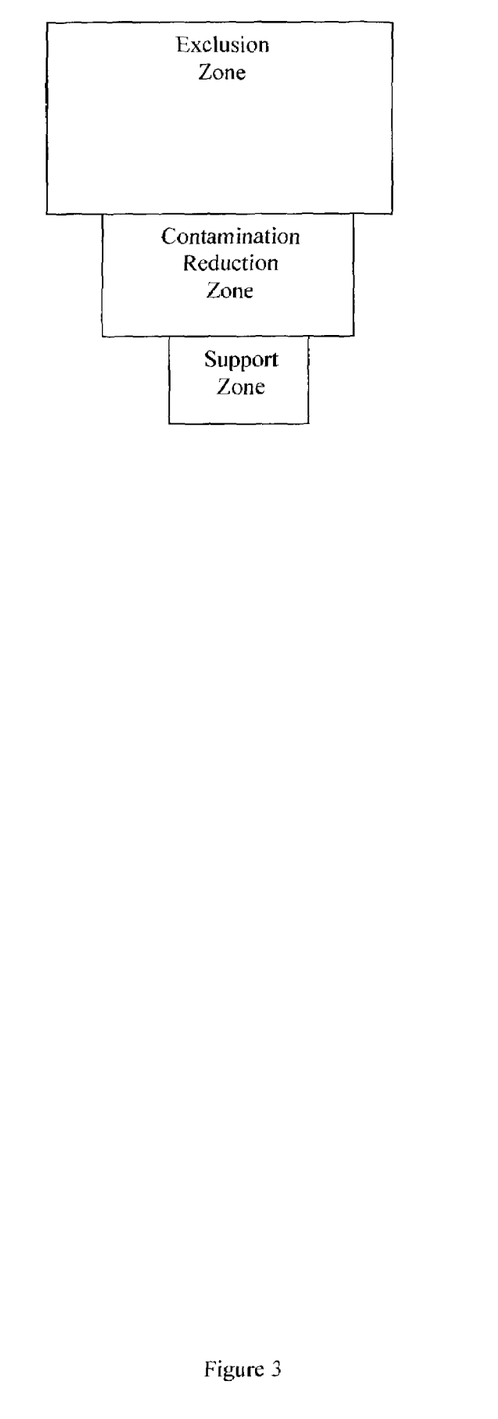
FIG. 3 is a block diagram illustrating the relative position of the exclusion zone, the contamination reduction zone and the support zone relative to one another.
Figure 4:
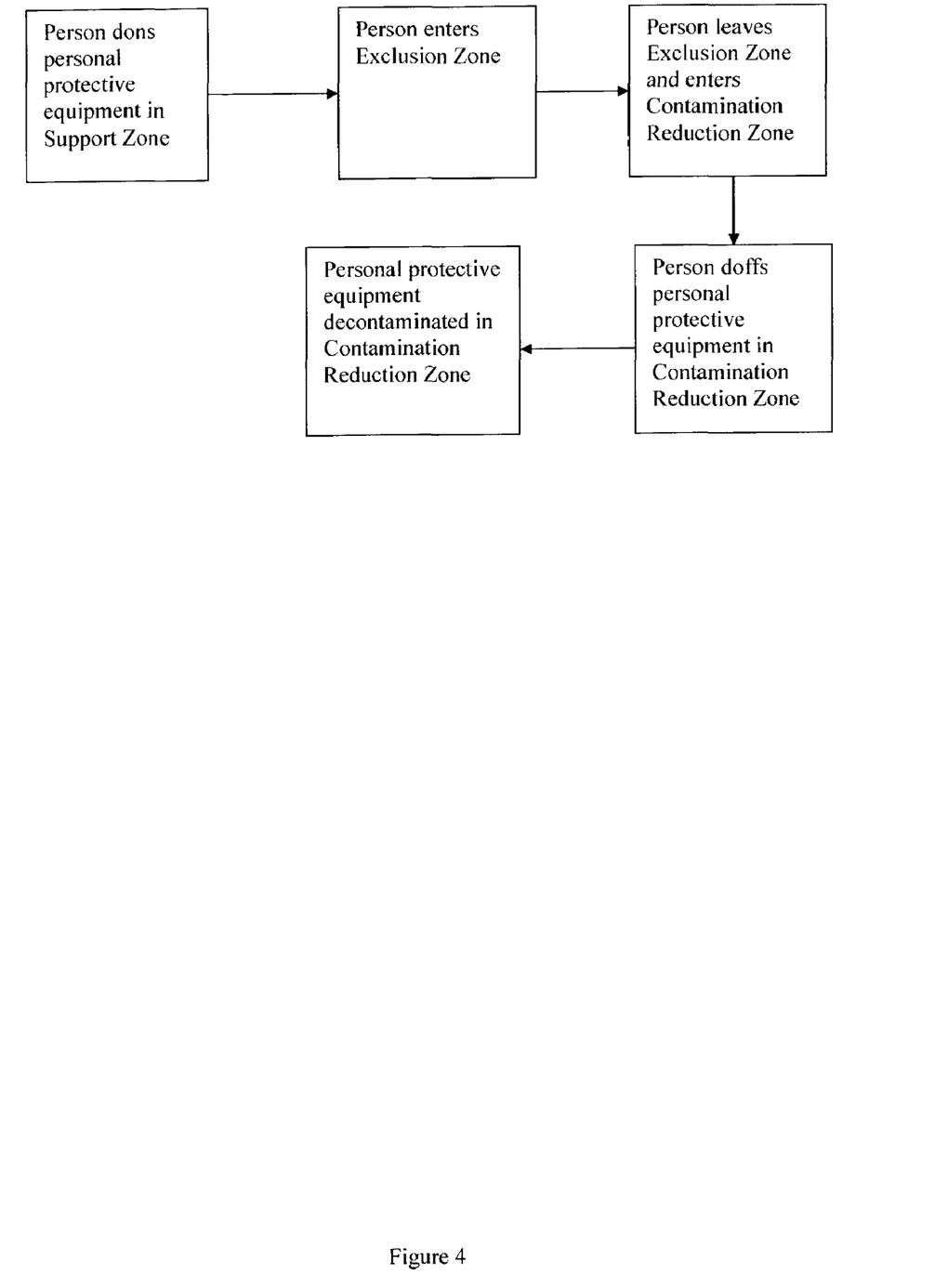
FIG. 4 is a flow chart illustrating the steps followed by a person seeking to enter an exclusion zone, exit therefrom, and decontaminate his or her personal protective equipment.

The general steps involved in the remediation of letter mail items suspected of possible exposure to a biological attack are depicted in the flow chart of FIG. 1. It should be recognized that some departure from the specific steps described herein, which reflect a preferred embodiment, may be possible without departing from the spirit or scope of the present invention. Thus, it may be possible to substitute one thicker bag for the two described herein, to use more than two bags, to eliminate the tray sleeve or to provide more than one tray sleeve, and so on.

Following irradiation, the boxes of mail are staged in a secure area for reworking operations. The secure area should be adequately ventilated to substantially prevent cross-contamination into other areas. The boxes and internal bags are then opened and placed in open trays to off-gas until VOCs, CO, and flammability levels are reduced to acceptable levels.

Where a vehicle has been used to transport mail items (or other goods) that are at least suspected of possible contamination as a result of a bioterrorism attack, it will be necessary to decontaminate the vehicle interior. For this process, it is first desired to create a suitable decontamination area. The features of such an area should include an underlying, impermeable layer that is strong enough to withstand the traction of tires. An additional desired feature is a barrier, such as a berm, to prevent the run-off of liquids utilized in the decontamination process and to allow their collection at the end of the process. (It should be apparent that run-off prevention could be accomplished in other ways, for example by providing an area with a sloped floor leading to one or more drain openings, or otherwise.) Commercially available household bleach solution containing 5.25% hypochlorite, when diluted 10:1 is effective in routine decontamination of surfaces and instruments after working with *B. anthracis*.

Once the vehicle is positioned within a suitable decontamination area, its interior should be sprayed using the decontamination solution. Once the spraying step is completed, the vehicle interior should be wiped down by hand, using clean cloths. The vehicle should then be permitted to stand exposed to the decontamination solution for approximately one hour, to allow sufficient contact time for the residual detergent to act. Next, the vehicle interiors should be thoroughly rinsed with clean tap water, and then allowed to air dry. The general steps associated with vehicle decontamination are illustrated in the flow chart of FIG. 2.

In order to undertake appropriate decontamination efforts with respect to a facility where a bioterrorism may have occurred, it is preferred to divide the suspected contamination site and its surrounding areas into at least three zones, as follows: (a) exclusion zone—this is the area that includes the source of the incident and which is therefore contaminated or is at least suspected of having been contaminated; (b) contamination reduction zone—this is the area adjacent to the exclusion zone and is utilized for the decontamination and rinsing of personal protective equipment (PPE); and (c) support zone—these are located at the entry points to the contamination reduction zone. The position of these three zones relative to one another—with the contamination reduction zone interposed between the support zone and the exclusion zone—is illustrated in the block diagram of FIG. 3.

The exclusion zone is the area where an attack is suspected to have occurred and where decontamination efforts are to be undertaken. Its boundaries are preferably determined from an initial post-attack assessment and is further based on an identification of hazards. Entry to the exclusion zone occurs only through the contamination reduction zone, and should be permitted only to persons wearing appropriate PPE's. It is preferred to clearly mark the exclusion zone with appropriate signage, so as to avoid accidental entry into the exclusion zone without proper equipment.

The contamination reduction zone is, as noted above, adjacent to the exclusion zone, and is a transition zone between the exclusion zone and the support zone. A person wearing a PPE (which has been donned in the support zone, discussed below) will pass through the contamination reduction zone and enter the exclusion zone. Such entrance preferably follows an inspection, which can occur in the support zone or in the contamination reduction zone, to ensure that the PPE is being worn correctly. The contamination reduction zone will also have a de-contamination facility to be utilized by persons exiting the exclusion zone, and is configured to permit the decontamination of PPE's. All PPE's should be removed before a worker exits the contamination reduction zone for the support zone. This method—donning of PEE in the support zone, entrance to the exclusion zone, exiting of the exclusion zone and passage into the contamination reduction zone, and decontamination of the PPE in the contamination reduction zone—is shown in the flow chart of FIG. 4.

The decontamination facility within the contamination reduction zone preferably consists of an enclosed tent system, having multiple (preferably four) stages. Within the tent system, and as more fully described below, decontamination, rinsing, and doffing of PPE's will occur.

The support zone is a clean zone, and is preferably a temporary structure, such as a trailer, that is not a fixed part of a facility containing a contamination site. In this manner, the support zone can be pre-configured in advance of a bioterrorism attack, and can be relatively quickly transported to the site and deployed for use. The support zone preferably contains, in addition to dressing facilities, equipment, the command post, and back-up personnel.

For persons needing to enter the contamination reduction zone and thereafter the exclusion zone, the support zone is used for donning PPE's. For those exiting the contamination reduction zone, the support zone is utilized for heat stress monitoring and showering. The support zone may also be utilized for storing respirators and for the charging of respirator power packs.

Persons exiting the exclusion zone and entering the contamination reduction zone must subject their PPE's to a decontamination process. The purpose of this process is to prevent exposure to the persons wearing the PPE's, and to prevent the spread of contamination to clean areas of the site.

A worker entering an exclusion zone will generally be wearing the following PPEs: safety goggles, Tyvek coveralls, two pairs of inner gloves, one pair of outer gloves, scrubs (under the PPE), steel-toed boots, booties, underclothing including a T-shirt, short pants and clean underwear, and a respirator. Tape will be used to seal the sleeve and pant leg openings. In some instances, the worker will also wear a hood.

As noted briefly above, it is preferred to divide the contamination reduction zone into four stages/areas, with different decontamination activities to occur in each area. Each stage/area should be defined by a separate tent, within the contamination reduction zone, and a person passes from area to area by exiting one tent and passing into the next. Some variation in the number of areas, and in the particular activities to occur in each, is possible, and may indeed be preferred depending on the circumstances.

In one embodiment, de-contamination proceeds as follows:

Area 1

The PPE is rinsed with a soap solution. Rinsing should be conducted twice—first the front of the suit, then the back, then the front again, and then the back again. If the worker was wearing a hood, this is rinsed as well. If not, the worker should lightly spray his or her head with the soap solution. The PPE should next be rinsed with water.

The tape is removed from the sleeve and pant leg openings. The worker also removes the PPE and the outer and the first pair of inner gloves. The PPE should be placed in a container and sprayed with a bleach solution, with the solution left thereon for approximately one hour contact time.

Area 2

In the second area, the worker will remove his or her inner scrubs by cutting and/or tearing them away. These should not be pulled over the head. The booties are also removed. The discarded scrubs should be placed in a container and sprayed with a bleach solution, with the solution left thereon for approximately one hour contact time. The discarded booties may be placed in a container with the scrubs, or may be placed in a separate container and sprayed with a bleach solution, with the solution left thereon for approximately thirty minutes contact time.

Area 3

In the next area, the worker removes his or her respirator (or other respiratory protection), as well as the second pair of inner gloves. The inner gloves are placed in a container and sprayed with a bleach solution, with the solution left thereon for approximately one hour contact time.

The respirator is placed into a bleach solution for 15 minutes. Its parts should be wiped down with the bleach solution, with the solution left thereon for an approximately forty-five minute contact time. Thereafter, the respirator should be rinsed with water.

Area 4

The next area is the showers area. All workers should shower before leaving the contamination reduction zone. Showering should be with soap and water.

In another embodiment, de-contamination proceeds as follows:

Area 1

The PPE is rinsed with a soap solution. Rinsing should be conducted twice—first the front of the suit, then the back, then the front again, and then the back again. If the worker was wearing a hood, this is rinsed as well. If not, the worker should lightly spray his or her head with the soap solution.

Area 2

In this area, the PPE is rinsed with water. The tape is removed from the sleeve and pant leg openings. The worker also removes the PPE and the outer and the first pair of inner gloves. The PPE should be placed in a container and sprayed with a bleach solution, with the solution left thereon for approximately one hour contact time.

Area 3

In the third area, the worker will remove his or her inner scrubs by cutting and/or tearing them away. These should not be pulled over the head. The booties are also removed. The discarded scrubs should be placed in a container and sprayed with a bleach solution, with the solution left thereon for approximately one hour contact time. The discarded booties may be placed in a container with the scrubs, or may be placed in a separate container and sprayed with a bleach solution, with the solution left thereon for approximately one hour contact time.

The worker removes his or her respirator (or other respiratory protection), as well as the second pair of inner gloves. The inner gloves are placed in a container and sprayed with a bleach solution, with the solution left thereon for approximately one hour contact time.

The respirator is placed into a bleach solution for 15 minutes. Its parts should be wiped down with the bleach solution, with the solution left thereon for an approximately forty-five minute contact time. Thereafter, the respiratory should be rinsed with water.

Area 4

The next area is the showers area. All workers should shower before leaving the contamination reduction zone. Showering should be with soap and water.

It should be recognized that the individual methods described herein, including remediation of goods (e.g., mail items), vehicles, facilities, and personal protective equipment could be utilized individually or as part of a comprehensive response to a biological attack. Moreover, while the invention has been particularly shown and described with reference to preferred embodiments thereof, it will be understood by those skilled in the art that the foregoing and other changes in form and details may be made therein without departing from the spirit and scope of the invention.

For example, additional packaging steps may be desired for mail items, or certain ones may be modified or eliminated, while still preserving the essential effectiveness of the irradiation treatment. Some departure from the contact times described herein may be permitted without unduly reducing the effectiveness of the bleach solution treatment. The concentration of the bleach solution may be altered slightly, to make it slightly more or slightly less concentrated, while maintaining effectiveness. It may be desired to wear additional personal protective equipment, beyond that described herein, which additional equipment would also need to be remediated. The contamination reduction zone could have more, or fewer, decontamination areas than are described herein.

What is claimed is:

1. A method for remediating the effects of a biological attack comprising the steps of:
    exposing mail items suspected of contamination from exposure to a biological agent to sufficient electron beam radiation to substantially decontaminate said mail items;
    segregating mail items by size and selecting mail items having a substantially letter size;
    positioning said substantially letter size mail items in a tray;
    sealing said tray with said letter size mail items therein into a letter tray sleeve;
    closing said letter tray sleeve;
    inserting said closed letter tray sleeve into a first polyvinyl bag having a thickness of between about 3 and about 6 mils;
    goosenecking an opening of said first polyvinyl bag and sealing said goosenecked opening with tape;
    inserting said goosenecked and sealed first polyvinyl bag into a second polyvinyl bag having a thickness of between about 3 and about 6 mils;
    goosenecking an opening of said second polyvinyl bag and sealing said goosenecked opening with tape;
    inserting said goosenecked and sealed second polyvinyl bag into a box; and
    sealing said box.

2. The method of claim 1 wherein said mail items are exposed to said electron beam radiation for a period of time between about 30 and about 60 minutes.

3. The method of claim 1 wherein said biological agent is the bacterium *Bacillus anthracis*.

4. The method of claim 1 further comprising the step of transporting said mail items in a vehicle from a first location to a second location, wherein said exposing step occurs at said second location.

5. The method of claim 4 further comprising the step of decontaminating said vehicle after said transporting step.

6. The method of claim 5 wherein said decontamination step comprises the steps of:
    creating a vehicle decontamination area;
    positioning said vehicle in said vehicle decontamination area; and
    spraying an interior of said vehicle with a bleach solution.

7. A method for remediating the effects of a biological attack comprising the steps of:
    exposing mail items suspected of contamination from exposure to a biological agent to sufficient electron beam radiation to substantially decontaminate said mail items;
    transporting said mail items in a vehicle from a first location to a second location, wherein said exposing step occurs at said second location; and
    decontaminating said vehicle after said transporting step, wherein said decontamination step comprises the steps of: creating a vehicle decontamination area; positioning said vehicle in said vehicle decontamination area; and spraying an interior of said vehicle with a bleach solution;
    wherein said vehicle decontamination area includes an underlying, impermeable layer that is strong enough to withstand the traction of tires and a barrier to prevent run-off of liquids utilized in the decontamination process and to allow their collection at the end of the process.

8. The method of claim 6 further comprising the steps of:
    wiping said vehicle interior;
    allowing said vehicle to stand for at least approximately one hour so as to permit sufficient contact time for said bleach solution to act;
    rinsing said vehicle interior with water; and
    allowing said vehicle interior to air dry.

9. A remediation method comprising the steps of:
    conducting remediation activities at a site where a biological attack may have occurred;
    establishing an exclusion zone with restricted access thereto;
    wherein said exclusion zone includes the site of the suspected biological attack;
    establishing a contamination reduction zone adjacent to said exclusion zone;
    wherein a person entering said exclusion zone or exiting from said exclusion zone does so through said contamination reduction zone;
    wherein said contamination reduction zone has located therein means for decontaminating personal protective equipment worn by said person exiting said exclusion zone; and
    establishing a support zone adjacent to said contamination reduction zone;
    wherein said support zone is a clean zone and wherein said support zone includes dressing facilities and equipment.

10. The method of claim 9 wherein said decontaminating means comprises an enclosed tent system defining a plurality of decontamination areas.

11. The method of claim 9 wherein said support zone is mobile.

12. The method of claim 9 wherein said support zone further has located therein a command post.

13. A remediation method in response to a biological attack on a facility comprising the steps of:
    entering an exclusion zone of a facility where a biological attack is at least suspected to have occurred;
    donning personal protective equipment prior to entering the exclusion zone;
    wherein said personal protective equipment includes an outer personal protective garment, an underlying clothing layer, a first inner pair of gloves, a second inner pair of gloves, an outer pair of gloves, and a foot covering;
    a person exiting said exclusion zone;
    a person decontaminating said personal protective equipment;
    wherein said decontamination step comprises the following steps:
    rinsing said outer personal protective garment with a soap solution;
    rinsing said outer personal protective garment with water;
    removing said outer personal protective garment;
    removing said outer pair of gloves and said first pair of inner gloves;
    spraying said outer personal protective garment with a bleach solution;
    removing said underlying clothing layer without pulling said underlying clothing layer over said person's head;
    removing said foot covering; spraying said underlying clothing layer with a bleach solution;

spraying said foot covering with a bleach solution; removing said second pair of inner gloves; and spraying said second pair of inner gloves with a bleach solution.

14. The method of claim 13 wherein said underlying clothing layer comprises scrubs.

15. The method of claim 13 wherein said personal protective equipment further comprises a respirator.

16. The method of claim 13 further comprising the step of leaving said bleach solution on said outer personal protective garment for approximately one hour.

17. The method of claim 13 further comprising the step of leaving said bleach solution on said underlying clothing layer for approximately one hour.

18. The method of claim 13 further comprising the step of leaving said bleach solution on said second pair of inner gloves for approximately one hour.

19. The method of claim 13 further comprising the step of leaving said bleach solution on said foot covering for at least approximately thirty minutes.

20. The method of claim 13 further comprising the step of said person showering with soap and water.

21. The method of claim 15 further comprising the steps of:
placing said respirator into said bleach solution for at least approximately 15 minutes;
wiping down parts of said respirator with said bleach solution;
leaving said bleach solution thereon for at least approximately 45 minutes; and
rinsing said respirator with water.

22. The method of claim 13 wherein said decontamination steps are performed in a contamination reduction zone adjacent to said exclusion zone, and wherein said contamination reduction zone is separated into a plurality of areas and wherein different decontamination steps are performed in different said areas.

23. The method of claim 7 wherein said mail items are exposed to said electron beam radiation for a period of time between about 30 and about 60 minutes.

24. The method of claim 7 wherein said biological agent is the bacterium *Bacillus anthracis*.

\* \* \* \* \*